United States Patent
Sunouchi et al.

[11] Patent Number: 5,357,973
[45] Date of Patent: Oct. 25, 1994

[54] MEASURING SYSTEM FOR VITAL MUSCLE ACTIVITY

[76] Inventors: Yujiro Sunouchi, 217, Fukuma-machi, Munakata-gun, Fukuoka-ken; Hiroshi Sakamoto, 14-403, Shimo-oori danchi, Oonojo-shi, Fukuoka-ken, both of Japan

[21] Appl. No.: 55,921

[22] Filed: Apr. 29, 1993

Related U.S. Application Data

[63] Continuation of Ser. No. 795,428, Nov. 20, 1991, abandoned.

[30] Foreign Application Priority Data

Nov. 30, 1990 [JP] Japan .................. 2-336659

[51] Int. Cl.⁵ .............................................. A61B 5/04
[52] U.S. Cl. ................................................. 128/733
[58] Field of Search ............... 128/733, 731, 696, 703, 128/705, 710, 777, 774

[56] References Cited

U.S. PATENT DOCUMENTS

| | | | |
|---|---|---|---|
| 3,657,646 | 4/1972 | Zmyslowski et al. | 128/733 |
| 4,155,352 | 5/1979 | Toglia et al. | 128/733 |
| 4,344,441 | 8/1982 | Radke | 128/733 |
| 4,355,645 | 10/1982 | Mitani et al. | 128/777 |
| 4,603,703 | 8/1986 | McGill et al. | 128/731 |
| 4,667,513 | 5/1987 | Konno | 73/379 |
| 4,827,934 | 5/1989 | Ekwall | 128/419 PG |

FOREIGN PATENT DOCUMENTS 2941991 4/1980 Fed. Rep. of Germany ...... 128/733

Primary Examiner—Stephen C. Pellegrino
Assistant Examiner—Guy V. Tucker
Attorney, Agent, or Firm—Kinney & Lange

[57] ABSTRACT

A measurement device which can easily measure and analyze the activity of the muscles of the living organism, for instance, measure the strength of occlusion of the masticatory muscles and duration thereof. The vital muscle activity measurement device comprises an amplifier means brought in contact with the muscles of a subject for detecting and amplifying a muscle current, an envelope forming means for forming an envelope waveform of the output of the amplifier means, and a timer means for determining the time for which the level of the envelope waveform obtained by the envelope forming means exceeds a preset reference level.

14 Claims, 3 Drawing Sheets

MEASURING SYSTEM FOR VITAL MUSCLE ACTIVITY

This is a continuation of application Ser. No. 07/795,428, filed Nov. 20, 1991, now abandoned.

BACKGROUND OF THE INVENTION

1. Field of the Invention

The present invention is related to a measuring system for the muscle activity of a living or vital organism, and particularly to a measuring system for the muscle activity of such as masticatory muscles, which can measure and analyze the change with time in the muscle activity or movement of the masticatory muscles of a human being to determine a set point of the measuring system for the muscle activity, and to a measuring system for the muscle activity of such as masticatory muscles, by which even ordinary people can easily and reliably measure and evaluate the activity or movement of muscles such as masticatory muscles on the basis of the reference value set by a specialist, such as a physician or a dentist, without any special training or skill.

2. Description of the Prior Art

Due to the recent rise in the general standard of living, the dietary habits of nations enjoying such a rise have changed and there is a strong that children prefer soft foods and dislike solid ones. For this reason, the development of the masticatory muscles of children has become very poor and various problems due to the insufficient or defective development of the masticatory muscles have been found.

If the masticatory muscles of children are insufficiently or defectively developed because they like to eat only soft foods, a vicious circle is easily introduced that further causes them to dislike solid foods. An extreme case was reported in which they could finally take only liquid foods.

Apart from such an extreme case, the number of children is increasing who have malocclusion of their maxillary and mandibular teeth, and thus have poorly aligned teeth. In addition, even if such children receive orthodontic treatment, it is often the result that the occlusal condition of the maxillary and mandibular teeth is not maintained and the original irregular teeth alignment is restored again because of the defective development of the masticatory muscles.

Moreover, if one has defectively developed masticatory muscles, the development of the jaw bones is also retarded, and not only are troubles caused in the jaw joint but also such a person cannot strongly occlude his masticatory muscles to close his mouth at times normal to do so, and as a result, he will always have open his mouth, or slobber in a worse case.

In addition, since it is thought that biting an object has a deep relationship with the development of the human brain, and that the use of masticatory muscles increases the $\lambda$-wave of the brain waves by which the ability to concentrate is increased, and thus the appropriate use and training of masticatory muscles are also desirable for the development of intelligence of children.

Conventionally, measuring the activity of vital muscles such as masticatory muscles with an electromyograph has been performed. In this case, usually the output waveform of the electromyograph obtained by setting electrodes on the vital muscles of a subject with the result displayed on an oscilloscope and/or recorded on an appropriate medium. A specialist such as a physician or a dentist observes the measurement result and determines the activity state of the masticatory muscles, and provides appropriate instructions or occlusion to the subject.

The above described prior art had the following problems. That is, to facilitate the development of masticatory muscles, for instance, it is required to continuously hold a strong occlusion state for a certain time in the training and to continue said training for a long period of time, there was a problem in that it was difficult to continue the training and the desired result of the training was not readily obtained, because the training could be provided only under the direction of a specialist. There are also similar problems for the other kinds of muscles.

Accordingly, development is desired of a system for measuring the muscle activity of such as masticatory muscles which can simply be used at home without requiring a attendance of the specialist and which also allows a patient to easily recognize the training effect, and/or of equipment which allows the setting of various measuring devices therefor to properly and easily be performed depending on a patient.

SUMMARY OF THE INVENTION

It is an object of the present invention to provide a system for measuring the muscle activity of a living or vital organism, which can easily measure and analyze the activity of the muscles of living organism, for instance, the strength of occlusion of the masticatory muscles and duration thereof.

It is another object of the present invention to provide a system for measuring the muscle activity of muscles such as masticatory muscles, which can use the results of the measurement and analysis to set a measuring reference value optimum for a particular patient.

It is a further object of the present invention to provide a system for measuring the muscle activity of muscles such as masticatory muscles, which can be easily used even at home without requiring the attendance of a specialist, and the training result obtained therewith can be also easily recognized.

The present invention comprises an amplifier means brought in contact with the muscles of a subject for detecting and amplifying a muscle current, an envelope forming means for forming an envelope waveform of the output of the amplifier means, and a timer means for counting the time during which the level of the envelope waveform obtained by the envelope forming means exceeds a preset reference level.

Also, the present invention is comprises another timer means for counting each intermittent time for which the level of the envelope waveform exceeds the preset reference level or/and counting the sum of the intermittent times.

The present invention further comprises a display device (e.g. a train or group of light-emitting elements) which changes the display mode depending on each intermittent time for which the reference level was exceeded, or/and on the sum of the intermittent times.

In addition, the present invention is characterized in that the above-described reference level can be variously preset and the time for which each reference level is exceeded is counted; and on the basis of the result of the counting, a specialist can accurately analyze and determine the activity of muscles such as masticatory muscles to set a reference level optimum for cure or training.

In the present invention, the envelope waveform of the output of the amplifier means for detecting and amplifying the muscle current of a living or vital organism is formed, and the times for which the level of the formed envelope waveform exceeds a plurality of preset reference levels are counted, stored and displayed for each reference level, so that not only the activity of the muscles of the living organism, for instance, the strength of occlusion by the masticatory muscles of the jaws or the duration thereof, can easily be measured and analyzed on the basis of the counting result, but also a reference value for discriminating the level of the envelope waveform that is optimum for a particular patient can be set using the analysis, Moreover, in the present invention, the envelope waveform of the output of the amplifier means for detecting and amplifying the muscle current is formed, and not only is the time for which the level of the formed envelope waveform exceeds the preset reference level counted and displayed, but also the specialist can optimally set such reference level on the basis of the result of the previously performed measurement of the activity of muscles such as masticatory muscles; for instance, measurement of the strength of occlusion of the jaws or the duration thereof thus the use thereof requires no particular skill and a subject himself can perform the training of his masticatory muscles while looking at the result of the time counting.

In addition, if the result of the measurement is visually displayed, for instance, if the number of energized light-emitting elements in a train of light-emitting elements is changed depending on the measurement result, discrimination between the results is further facilitated. Also, the ratio of the training time to the time for which the reference level is exceeded can be calculated and displayed thus by performing the training while the subject is looking at results of such various countings and calculations, the training can be performed while maintaining the subject's interest and a continuous long-term training also becomes easy for the subject.

DETAILED DESCRIPTION OF THE PREFERRED EMBODIMENT

Figure 1:
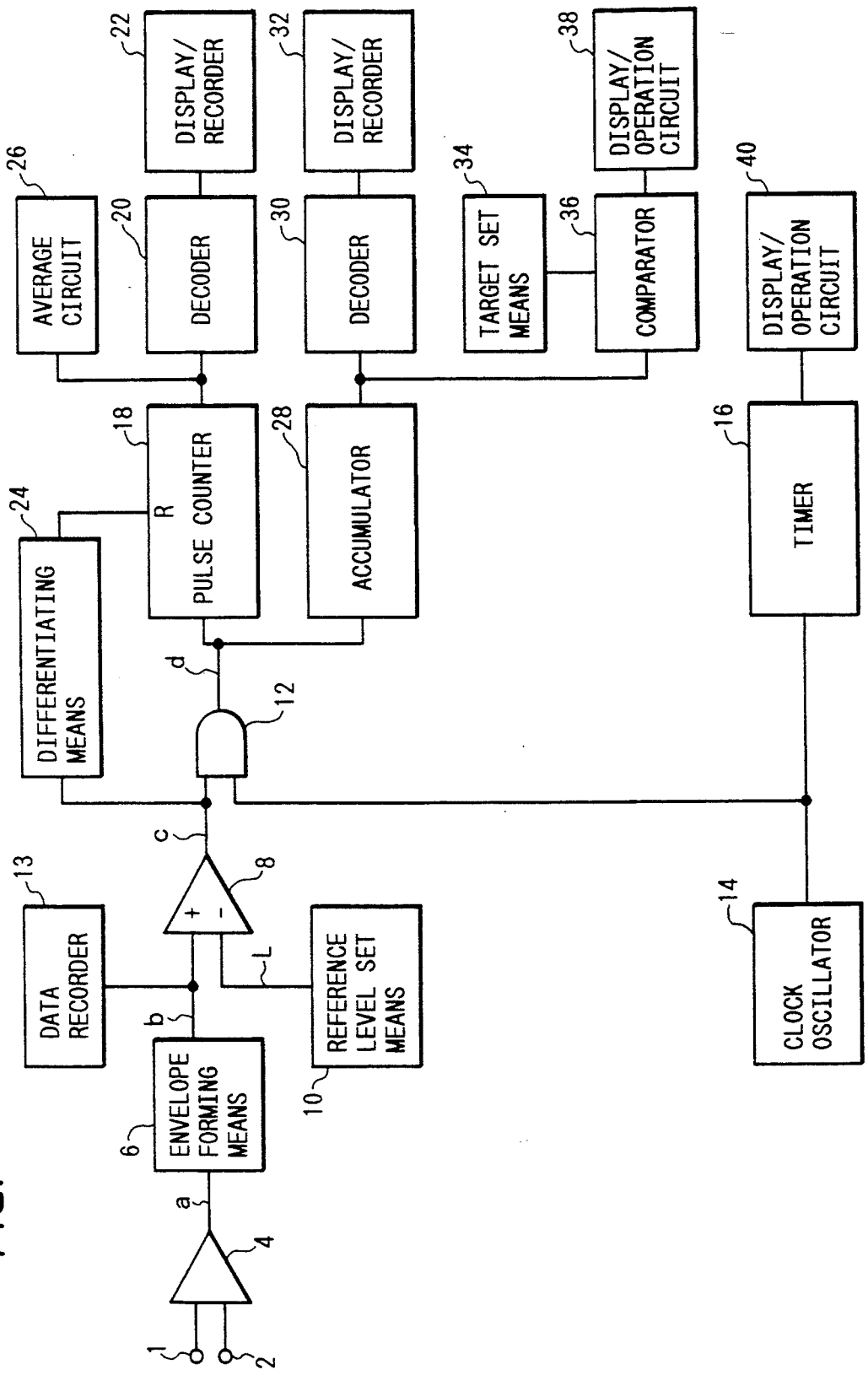
FIG. 1 is a block diagram of an embodiment of the present invention.

Now, the present invention is described in detail with reference to the drawings. FIG. 1 is a block diagram of an embodiment in which the present invention is applied to the measurement of the activity of masticatory muscles.

Contact electrodes 1 and 2 are appropriately attached to the masticatory muscle portions of the cheeks of a subject, and their detection outputs are supplied to an amplifier 4. For the contact electrodes 1 and 2 and the amplifier 4, a conventional electromyograph can be used. A muscle current is induced in the masticatory muscle is to be detected by the contact electrodes and amplified when the subject masticates something. The muscle current is an alternating current of the order of 300 Hz, and its magnitude or amplitude is substantially proportional to the occlusal force.

Figure 2:
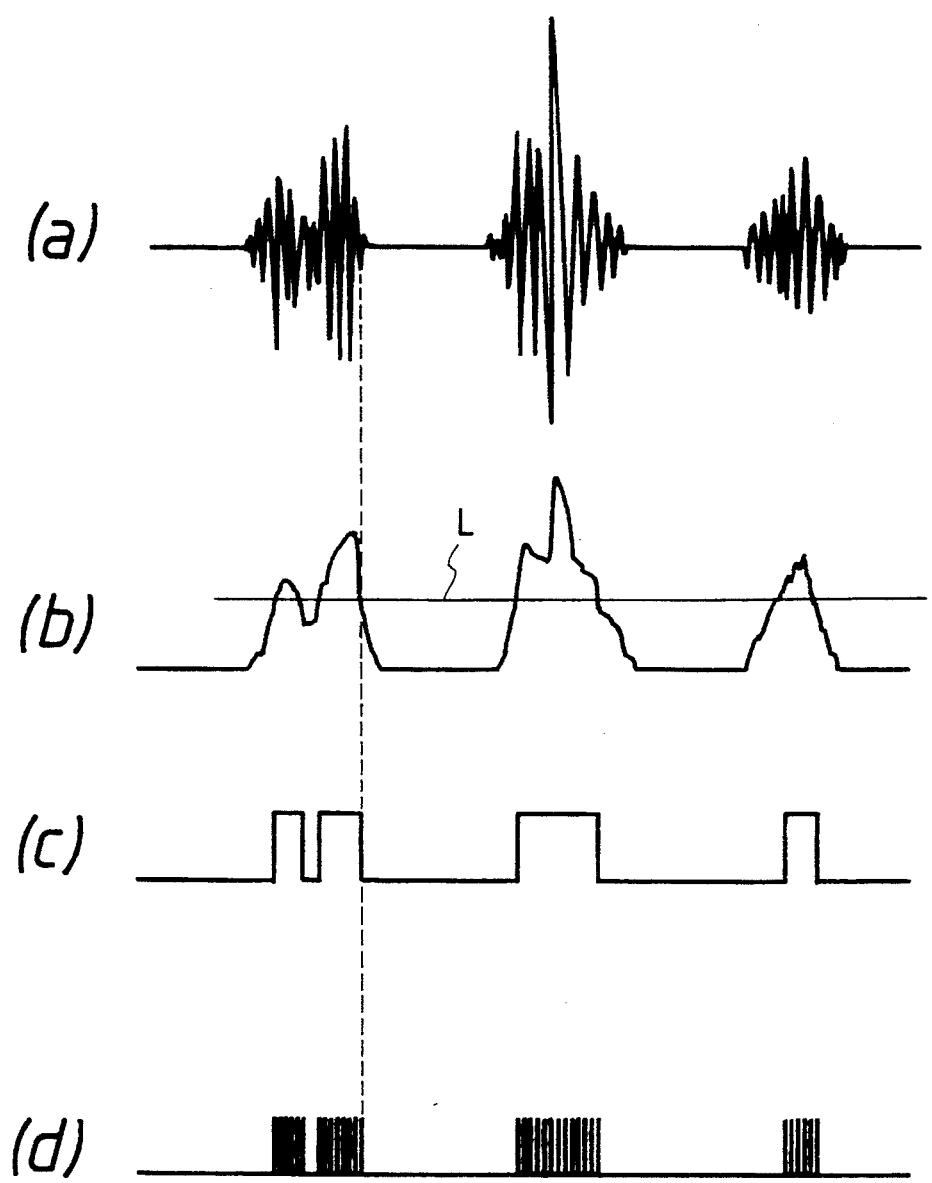
FIG. 2 shows four waveform diagrams for explaining the operation of the embodiment of the present invention.

FIG. 2(a) shows an example of the output waveform of the amplifier 4 when the subject intermittently occludes his teeth. The output of the amplifier 4 is provided to an envelope forming means 6, and an envelope signal of the waveform (a) is obtained as its output as shown in FIG. 2(b). The envelope signal is supplied to the first input of a comparator 8. The second input of The comparator 8, has a reference level signal from a reference level setting means 10 is supplied thereto. The envelope signal may also be supplied to a data recorder 13 which is preferably portable.

Accordingly, if the reference level is set to be, for instance, L in FIG. 2(b), the output of the comparator 8 is a rectangular wave as shown in FIG. 2(c). As is apparent, the rectangular wave of the waveform (c) indicates at non-zero values thereof that the subject bit an object or occluded his teeth during such occurrences with a force stronger than a certain set level.

The output rectangular wave of the comparator 8 is provided to the first input of an AND circuit 12, and a clock signal from a clock oscillator 14 is provided to the second input of the AND circuit 12. Thus, at the output of the AND circuit 12, segments of the clock signal from clock oscillator 14 appears only during these times when the rectangular wave provides by the comparator 8, has other than a zero value and the cycles in the segments of the clock signal provided at the output of AND circuit 12 are counted by a pulse counter 18 and an accumulating counter 28.

A differential circuit 24 differentiates the rectangular wave output of the comparator 8 and supplies negative one of the resulting pulses to the reset terminal R of the pulse counter 18. The pulse counter 18 counts the number of the pulses or cycles generated in the clock signal segments during the non-zero time in the of each rectangular wave to determine the duration for each non-zero time in the rectangular wave as shown in FIG. 2(d).

A display and recording means 22 consists of a multiplicity of light-emitting elements such as LED's, for instance, which are unidimensionally arranged. A decoder 20 associates the count value of pulse counter 18 with the number of the light-emitting elements to be lit on the display, and for instance, it operates so that the more the count value is, the greater the number of light-emitting elements lit. Further, the light-emitting elements may be made to gradually change their color tone in response to the distance from a reference point similar to the colors of a rainbow, for instance.

Clearly, the larger the occlusal force, the greater the number of clock pulses passing through the AND circuit 12, thereby causing the number of the light-emitting elements to be lit so that the subject can very easily recognize visually the degree of occlusal force. The strength or pitch of a sound may of course be employed instead of the visual display.

An average value circuit 26 is used to average the count value of the pulse counter 18 for a predetermined length of time or a predetermined number of pulses, by which the average occlusal force can be known. The average value can also be displayed by providing means similar to the display and recording means 22 and the decoder 20.

An accumulating counter 28 is used to accumulate the total number of clock pulses passing through the AND circuit 12 for one day, for instance, by which the sum of the times for which the subject bit the object or occluded his teeth can be measured. A decoder 30 and a display and recording means 32 operate in a manner similar to the decoder 20 and the display/recording means 22.

In a target setting means 34, a target value of the total sum times mentioned above is preset, and is compared in a comparator 36 with the output of the accumulating counter 28. The comparator 36 provides an output when the sum of the pulses or cycles for the times in which the subject has bitten the object or occluded his teeth with a force greater than the given set level reaches the target value. This allows a display and operation circuit 38 to display that the target value was reached and/or stops the system.

A timer 16 counts the output pulses of the clock oscillator 14 and measures the duration time of the training. When a preset time has elapsed, the timer 16 counts over and drives a display and operation circuit 40 to display that the target time has been reached and/or stops the system as in the case where the comparator 36 has generated its output.

Figure 3:
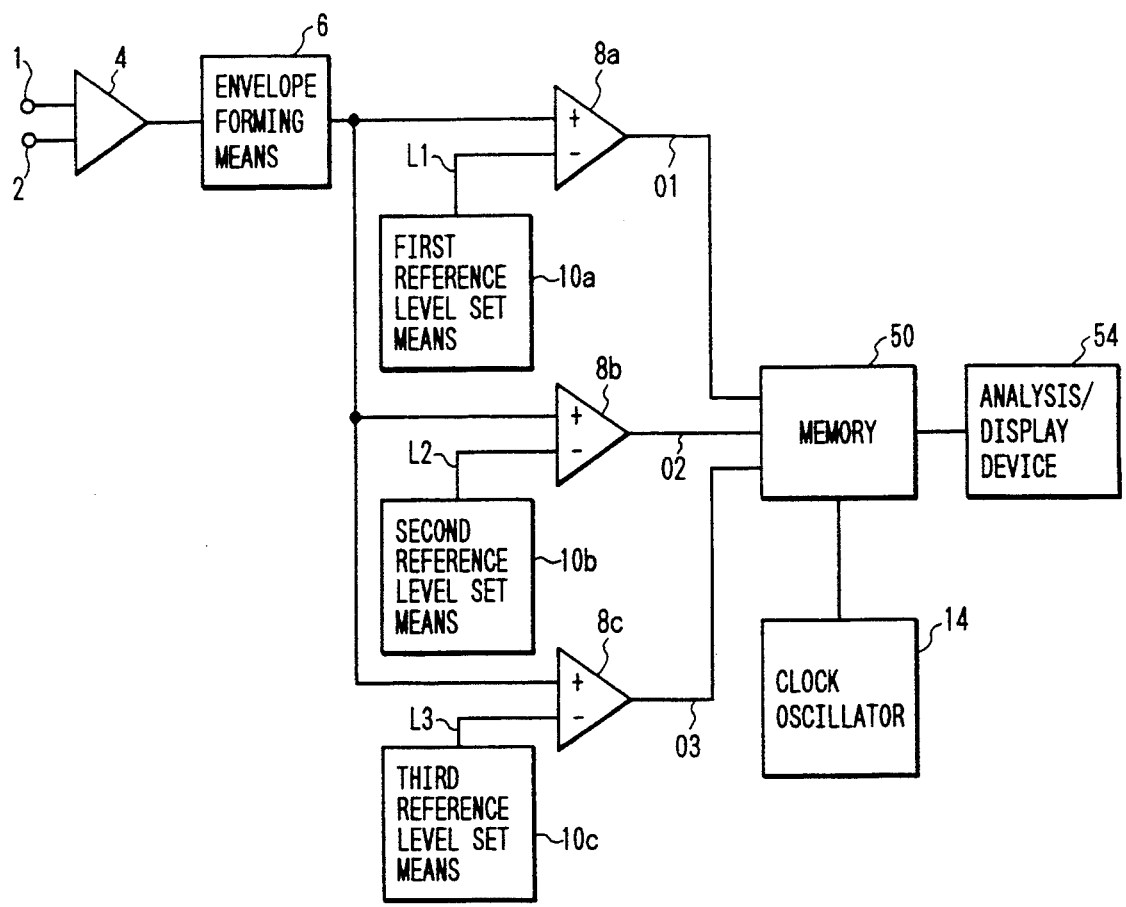
FIG. 3 is a block diagram of another embodiment of the present invention.

FIG. 3 is a block diagram showing an example of a system for measuring the activity of a muscle such as masticatory muscles, which is suitable for a specialist such as a physician or a dentist to easily measure and analyze the activity of the muscles such as thereof masticatory muscles of a patient, as for instance, measuring the occlusion strength of his jaws or the duration thereof, or to perform a preliminary measurement for setting the value of the reference level setting means 10 in the system of FIG. 1, namely, the discriminating value for the level of the envelope waveform optimum to the particular patient by using the result of the analysis. In the same figure, the same reference numerals as FIG. 1 represent the same or identical portions.

Figure 4:
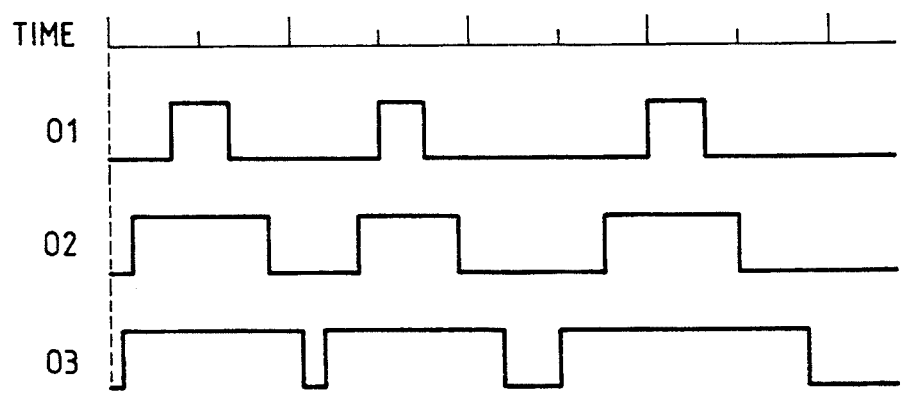
FIG. 4 is an exemplary view showing the storage state of the memory of FIG. 3.

In this embodiment, there are provided three comparators 8a–8c to which first to third reference level setting means 10a–10c are connected, respectively. The reference values to be set in the individual reference level setting means are, of course, different from each other. Here, if it is supposed that the set level L1 of the first reference level setting means 10a is highest and the set levels L2 and L3 of the second and third level setting means 10b and 10c become lower in this order, the corresponding rectangular wave outputs 01–03 of the individual comparators 8a–8c are, for instance, as shown in FIG. 4.

The outputs from the individual comparators 8a–8c are stored in memory 50 along with the signal clock from clock oscillator 14. FIG. 4 conceptually shows the memory state of memory 50. The numbers of the comparators and reference level setting means are not limited to three, but any plurality of them are acceptable.

The data stored in memory 50 is transferred to analysis and display device 54 where they are analyzed according to a predetermined technique or algorithm. For instance, by comparison of the occlusion state, including the variation with time and the strength distribution thereof, in the, and difference in distribution among individuals for normal people to the same kind of data obtained on a patient, the muscle activity of the patient can be determined and diagnosed, or the reference level (of reference level setting means 10 fin FIG. 1) for training and/or cure can be determined.

As apparent from the above description, in accordance with the present invention, by gathering various rectangular wave signals, through discrimination between portions of the output waveform with a plurality of reference levels, and analyzing and determining them, the muscle activity of a live or vital organism, for instance, the occlusion strength of the jaws and the duration of the occlusion can easily be measured and analyzed The use of the results of the measurement and analysis allows the setting of the reference value for the treatment and training optimum for a particular patient.

Also, in accordance with the present invention, the time for which the patient has bitten with a force stronger than the given set value can visually be recognized not only from the display of the counter but also from the lighting state of linearly arranged LED's, and thus help that the patient himself to determine his own occlusion force, continue the training, and make an evaluation without any particular direction by a specialist.

In consequence, it is easy for the patient or subject to adjust the occlusal force while looking at the display of the examination result and try to bite with a force greater than the set value, and he can thereby accomplish the increasing of his muscular strength by training.

In addition, the set value can properly be set according to the condition of the subject so that optimum setting is easy. Also, it is possible to measure the percentage of the time for which the subject has bitten with an occlusal force larger than the set value during his training, to count the total time of the training and/or to calculate and display the ratio of the training time or the time for which he has bitten with the occlusal force larger than the set value to the total time, all of which are useful.

Since the system of the present invention is simple and can be made in small size for portable use, one can always carry it with him for training at all times and in many places, a better training effect can be expected.

Although the present invention has been described above by taking as an example the case in which it is used for measuring the activity of masticatory muscles, it will easily be understood that the present invention can also be applied to the measurement of the activity of the muscles in general living or vital organisms.

What is claimed is:

1. A system for measuring the muscle activity of a living organism comprising:

a muscle current detection means suitable for being brought into electrical contact with a subject living organism adjacent a selected muscle thereof for detecting muscle current to provide a corresponding output signal waveform having therein at least oscillatory episode with oscillation peaks therein of various amplitudes.

an envelope waveform forming means for forming envelope waveforms representing muscle activity with each being formed for a corresponding one of those oscillatory episodes occurring in the output waveform of the muscle current detection means and based on the peak amplitude therein, a timer means for measuring the duration of time for which the values of each envelope waveform formed by the envelope wave forming means are beyond a selected reference level to indicate those durations that said muscle activity was beyond a corresponding muscle activity level, and a display means for providing an indication of the duration of time measured for each envelope waveform.

2. The system of claim 1 wherein display means includes a plurality of light-emitting elements and which can change the lighting states of the individual light-emitting elements depending on the durations of times measured by the timer means.

3. The system of claim 2 wherein the number of light-emitting elements to have light intensity changes as the lighting state changes depends on the durations of times measured by the timer means.

4. The system of claim 2 wherein the emissive color tone of the light-emitting elements in selected lighting states is changed depending on the durations of times measured by the timer means.

5. The system of claim 2 wherein the timer means comprises a comparator for comparing the values of each envelope waveform to a selected reference level to provide an output signal at an output thereof indicating relative magnitudes thereof, a clock signal source providing a clock signal having clock periodic pulses therein, an AND logic gate circuit to which the output of the comparator and the output of the clock signal source are coupled to thereby provide gate output signal periodic pulses at an output thereof during time durations determined by the comparator output signal, and a counter means coupled to the AND logic gate circuit output for counting the gate output signal periodic pulses.

6. The system of claim 5 wherein the counter means for counting the clock signal is reset each time the output signal of the comparator changes toward a selected value.

7. The system of claim 2 wherein the timer means comprises a comparator for comparing the values of each envelope waveform to a selected reference level to provide an output signal at an output thereof indicating relative magnitudes thereof, a clock signal source providing a clock signal having clock periodic pulses therein, an AND logic gate circuit to which the output of the comparator and the output of the clock signal source are coupled to provide gate output signal periodic pulses at an output thereof during the time durations determined by the comparator output signal, and an accumulator means coupled to the AND logic gate circuit output for accummulatively counting the gate output signal periodic pulses.

8. The system of claim 7 further comprising a second comparator for comparing the count value of the accumulator means to a predetermined target value, and a display and operation means which responds to the output of the second comparator.

9. The system of claim 1 wherein the timer means comprises a comparator for comparing the values of each envelope waveform to a selected reference level to provide an output signal at an output thereof indicating relative magnitude thereof, a clock signal source providing a clock signal having clock periodic pulses therein, an AND logic gate circuit to which the output of the comparator and the output of the clock signal source are coupled to thereby provide gate output signal periodic pulses at an output thereof during time durations determined by the comparator output signal, and a counter means coupled to the AND logic gate circuit output for counting the gate output signal periodic pulses.

10. The system of claim 9 wherein the counter means for counting the clock signal is reset each time the output signal of the comparator changes toward a selected value.

11. The system of claim 1 wherein the timer means comprises a comparator for comparing the values of each envelope waveform to a selected reference level to provide an output signal at an output thereof indicating relative magnitudes thereof, a clock signal source providing a clock signal having clock periodic pulses therein, an AND logic gate circuit to which the output of the comparator and the output of the clock signal source are coupled to provide gate output signal periodic pulses at an output thereof during time durations determined by the comparator output signal, and an accumulator means coupled to the AND logic gate circuit output for accumulatively counting the gate output signal periodic pulses.

12. The system of claim 11 further comprising a second comparator for comparing the count value of the accumulator means to a predetermined target value, and a display and operation means which responds to the output of the second comparator.

13. A system for measuring the muscle activity of a living organism comprising:

a muscle current detection means suitable for being brought into electrical contact with a subject living organism adjacent a selected muscle thereof for detecting muscle current to provide a corresponding output signal waveform having therein at least one oscillatory episode with oscillation peaks therein of various amplitudes, an envelope waveform forming means for forming envelope waveforms representing muscle activity with each being formed for a corresponding one of those oscillatory episodes occurring in the output waveform of the muscle current detection means and based on said peak amplitudes therein, a plurality of timer means for respectively measuring the durations of times for which the values of each envelope waveform formed by the envelope wave forming means exceeds a corresponding one of a plurality of selected reference levels of differing values to indicate those durations that said muscle activity was beyond corresponding muscle activity levels, and a display means for providing an indication of the durations of times measured for each envelope waveform.

14. The system of claim 13 wherein each of the timer means comprises a comparator for comparing the values of each envelope waveform to a corresponding selected reference level to provide an output signal at an output thereof indicating relative magnitudes therefor with each of these selected reference levels differing from one another, and an AND logic gate circuit to which the output of the comparator is coupled, and with there also being a clock signal source providing a clock signal having clock periodic pulses therein which is coupled to each of the AND logic gate circuits such that they each provide gate output signal periodic pulses at an output thereof during time durations determined by the corresponding comparator output signal, and further comprising a memory means coupled to each of the AND logic gate circuits for storing at least portions of the gate output signals thereof.

* * * * *

UNITED STATES PATENT AND TRADEMARK OFFICE
CERTIFICATE OF CORRECTION

PATENT NO. : 5,357,973
DATED : October 25, 1994
INVENTOR(S) : YUJIRO SUNOUCHI, HIROSHI SAKAMOTO It is certified that error appears in the above-indentified patent and that said Letters Patent is hereby corrected as shown below:

Col. 1, line 27, after "strong", insert --tendency--

Col. 6, line 50, after "least", insert --one--

Col. 6, line 59, delete "amplitude", insert --amplitudes--

Col. 7, line 1, after "wherein", insert --the--

Signed and Sealed this

Twenty-fifth Day of April, 1995

Attest:

BRUCE LEHMAN

*Attesting Officer*    *Commissioner of Patents and Trademarks*